United States Patent
Eno et al.

(10) Patent No.: US 6,916,304 B2
(45) Date of Patent: *Jul. 12, 2005

(54) TRANSMYOCARDIAL IMPLANT WITH FLOW REDUCTION

(75) Inventors: Robert A. Eno, Plymouth, MN (US); Guy P. Vanney, Blaine, MN (US)

(73) Assignee: Percardia, Inc., Merrimac, NH (US)

( * ) Notice: Subject to any disclaimer, the term of this patent is extended or adjusted under 35 U.S.C. 154(b) by 256 days.

This patent is subject to a terminal disclaimer.

(21) Appl. No.: 10/155,926

(22) Filed: May 23, 2002

(65) Prior Publication Data

US 2002/0143285 A1 Oct. 3, 2002

Related U.S. Application Data

(63) Continuation of application No. 09/304,730, filed on May 4, 1999, now Pat. No. 6,409,697.

(51) Int. Cl.$^7$ .......................... A61M 5/00; A61M 29/00; A61F 2/06; A61F 2/02; A61B 17/08
(52) U.S. Cl. ............................. 604/9; 604/8; 623/1.15; 623/11.11; 606/153; 606/194
(58) Field of Search ............................... 604/8–10, 264, 604/523; 128/898; 623/11.11, 1.1, 1.23, 1.44, 1.3–1.31, 1.36–1.37, 1.46, 1.49, 66.1, 902–903; 606/153, 194

(56) References Cited

U.S. PATENT DOCUMENTS

| | | |
|---|---|---|
| 4,546,499 A | 10/1985 | Possis et al. |
| 4,953,553 A | 9/1990 | Tremulis |
| 5,193,546 A | 3/1993 | Shaknovich |
| 5,258,008 A | 11/1993 | Wilk |
| 5,287,861 A | 2/1994 | Wilk |
| 5,330,486 A | 7/1994 | Wilk |
| 5,344,426 A | 9/1994 | Lau et al. |
| 5,389,096 A | 2/1995 | Aita et al. |
| 5,409,019 A | 4/1995 | Wilk |

(Continued)

FOREIGN PATENT DOCUMENTS

| | | |
|---|---|---|
| AU | 757647 | 2/2003 |
| EP | 0 732 088 A2 | 9/1996 |

(Continued)

OTHER PUBLICATIONS

US 6,331,185, 12/2001, Gambale et al. (withdrawn)
Tweden et al. *Ventriculocoronary Artery Bypass (VCAB), a Novel Approach to Myocardial Revascularization.*

(Continued)

*Primary Examiner*—Patricia Bianco
(74) *Attorney, Agent, or Firm*—Finnegan, Henderson, Farabow, Garrett & Dunner LLP

(57) ABSTRACT

A transmyocardial implant establishes a blood flow path through a heart wall between a heart chamber and a lumen of a coronary vessel on the heart wall. The implant includes a hollow conduit having an open first end and an open second end. The conduit is dimensioned so as to extend at least from the vessel through said heart wall and into said chamber. The conduit has a conduit wall defining a blood flow pathway within an interior of said conduit between the first and second ends. The first and second ends are mutually positioned for the first end to reside within the vessel and opposing a wall of the vessel when the conduit is placed within the heart wall with the second end protruding into the chamber. The conduit wall is formed of a material sufficiently rigid to resist deformation and closure of the pathway in response to contraction of the heart wall. A flow restriction is formed in the pathway for reducing a discharge velocity of blood flow discharged from the first end.

23 Claims, 1 Drawing Sheet

U.S. PATENT DOCUMENTS

| | | |
|---|---|---|
| 5,429,144 A | 7/1995 | Wilk |
| 5,470,320 A | 11/1995 | Tiefenbrun et al. |
| 5,554,119 A | 9/1996 | Harrison et al. |
| 5,593,434 A | 1/1997 | Williams |
| 5,618,299 A | 4/1997 | Khosravi et al. |
| 5,655,548 A | 8/1997 | Nelson et al. |
| 5,662,124 A | 9/1997 | Wilk |
| 5,733,267 A | 3/1998 | Del Toro |
| 5,755,682 A | 5/1998 | Knudson et al. |
| 5,758,663 A | 6/1998 | Wilk et al. |
| 5,807,384 A | 9/1998 | Mueller |
| 5,810,836 A | 9/1998 | Hussein et al. |
| 5,824,071 A | 10/1998 | Nelson et al. |
| 5,830,222 A | 11/1998 | Makower |
| 5,876,373 A | 3/1999 | Giba et al. |
| 5,878,751 A | 3/1999 | Hussein et al. |
| 5,885,259 A | 3/1999 | Berg |
| 5,908,028 A | 6/1999 | Wilk |
| 5,908,029 A | 6/1999 | Knudson et al. |
| 5,922,022 A | 7/1999 | Nash et al. |
| 5,925,012 A | 7/1999 | Murphy-Chutorian et al. |
| 5,931,848 A | 8/1999 | Saadat |
| 5,935,161 A | 8/1999 | Robinson et al. |
| 5,938,632 A | 8/1999 | Ellis |
| 5,944,019 A | 8/1999 | Knudson et al. |
| 5,968,064 A | 10/1999 | Selmon et al. |
| 5,971,993 A | 10/1999 | Hussein et al. |
| 5,976,155 A | 11/1999 | Foreman et al. |
| 5,980,533 A | 11/1999 | Holman |
| 5,980,548 A | 11/1999 | Evans et al. |
| 5,984,956 A * | 11/1999 | Tweden et al. ............. 623/1.36 |
| 5,997,525 A | 12/1999 | March et al. |
| 5,999,678 A | 12/1999 | Murphy-Chutorian et al. |
| 6,004,261 A | 12/1999 | Sinofsky et al. |
| 6,004,347 A | 12/1999 | McNamara et al. |
| 6,007,543 A | 12/1999 | Ellis et al. |
| 6,010,449 A | 1/2000 | Selmon et al. |
| 6,026,814 A | 2/2000 | LaFontaine et al. |
| 6,029,672 A | 2/2000 | Vanney et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,045,565 A | 4/2000 | Ellis et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower |
| 6,071,292 A | 6/2000 | Makower et al. |
| 6,076,529 A * | 6/2000 | Vanney et al. ............. 128/898 |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |
| 6,102,941 A | 8/2000 | Tweden et al. |
| 6,113,823 A * | 9/2000 | Eno ............................. 264/81 |
| 6,120,520 A | 9/2000 | Saadat et al. |
| 6,123,682 A | 9/2000 | Knudson et al. |
| 6,126,654 A | 10/2000 | Giba et al. |
| 6,132,405 A * | 10/2000 | Nilsson et al. ............. 604/264 |
| 6,132,451 A | 10/2000 | Payne et al. |
| 6,139,541 A | 10/2000 | Vanney et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,165,188 A | 12/2000 | Saadat et al. |
| 6,171,251 B1 | 1/2001 | Mueller et al. |
| 6,182,668 B1 * | 2/2001 | Tweden et al. ............. 128/898 |
| 6,186,972 B1 | 2/2001 | Nelson et al. |
| 6,190,353 B1 | 2/2001 | Makower et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,324 B1 | 3/2001 | Crittenden |
| 6,200,311 B1 | 3/2001 | Danek et al. |
| 6,203,556 B1 | 3/2001 | Evans et al. |
| 6,213,126 B1 | 4/2001 | LaFontaine et al. |
| 6,214,041 B1 | 4/2001 | Tweden et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,418 B1 | 6/2001 | Ahern et al. |
| 6,253,769 B1 | 7/2001 | LaFontaine et al. |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,728 B1 | 9/2001 | Phelps et al. |
| 6,302,875 B1 | 10/2001 | Makower et al. |
| 6,322,548 B1 | 11/2001 | Payne et al. |
| 6,330,884 B1 | 12/2001 | Kim |
| 6,350,248 B1 | 2/2002 | Knudson et al. |
| 6,361,519 B1 | 3/2002 | Knudson et al. |
| 6,363,938 B2 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,409,697 B2 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,454,760 B2 | 9/2002 | Vanney |
| 6,454,794 B1 | 9/2002 | Knudson et al. |
| 6,458,092 B1 | 10/2002 | Gambale et al. |
| 6,458,323 B1 | 10/2002 | Boekstegers |
| 6,475,226 B1 | 11/2002 | Belef et al. |
| 6,475,244 B2 | 11/2002 | Herweck et al. |

| | | |
|---|---|---|
| 6,482,220 B1 | 11/2002 | Mueller |
| 6,491,689 B1 | 12/2002 | Ellis et al. |
| 6,491,707 B2 | 12/2002 | Makower et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,524,323 B1 | 2/2003 | Nash et al. |
| 6,544,230 B1 | 4/2003 | Flaherty |
| 6,559,132 B1 | 5/2003 | Holmer |
| 6,561,998 B1 | 5/2003 | Roth et al. |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,575,168 B2 | 6/2003 | LaFontaine et al. |
| 6,579,311 B1 | 6/2003 | Makower |
| 6,599,304 B1 | 7/2003 | Selmon et al. |
| 6,605,053 B1 | 8/2003 | Kamm et al. |
| 6,610,100 B2 | 8/2003 | Phelps et al. |
| 6,613,081 B2 | 9/2003 | Kim et al. |
| 6,616,675 B1 | 9/2003 | Evard et al. |
| 6,638,247 B1 | 10/2003 | Selmon et al. |
| 6,638,293 B1 | 10/2003 | Makower et al. |
| 6,641,610 B2 | 11/2003 | Briefs et al. |
| 6,651,670 B2 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,694,983 B2 | 2/2004 | Wolf et al. |
| 6,709,425 B2 | 3/2004 | Gambale et al. |
| 6,709,444 B1 | 3/2004 | Makower |
| 6,719,770 B2 | 4/2004 | Laufer et al. |
| 6,726,677 B1 | 4/2004 | Flaherty et al. |
| 6,746,464 B1 | 6/2004 | Makower |
| 2001/0000041 A1 | 3/2001 | Selmon et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012948 A1 | 8/2001 | Vanney |
| 2001/0014813 A1 | 8/2001 | Saadat et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027341 A1 | 10/2001 | Shmulewitz et al. |
| 2001/0034547 A1 | 10/2001 | Hall et al. |
| 2001/0037117 A1 | 11/2001 | Gambale et al. |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0047165 A1 | 11/2001 | Makower et al. |
| 2001/0049523 A1 | 12/2001 | DeVore et al. |
| 2001/0053932 A1 | 12/2001 | Phelps et al. |
| 2002/0002349 A1 | 1/2002 | Flaherty et al. |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0049486 A1 | 4/2002 | Knudson et al. |
| 2002/0058897 A1 | 5/2002 | Remati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0077566 A1 | 6/2002 | Laroya et al. |
| 2002/0077654 A1 | 6/2002 | Javier, Jr. et al. |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095206 A1 | 7/2002 | Addonizio et al. |
| 2002/0100484 A1 | 8/2002 | Hall et al. |
| 2002/0111672 A1 | 8/2002 | Kim et al. |
| 2002/0123698 A1 | 9/2002 | Garibotto et al. |
| 2002/0143289 A1 | 10/2002 | Ellis et al. |
| 2002/0144696 A1 | 10/2002 | Sharkawy et al. |
| 2002/0161424 A1 | 10/2002 | Rapacki et al. |
| 2002/0165479 A1 | 11/2002 | Wilk |
| 2002/0165606 A1 | 11/2002 | Wolf et al. |
| 2002/0179098 A1 | 12/2002 | Makower et al. |
| 2002/0183716 A1 | 12/2002 | Herweck et al. |
| 2002/0193782 A1 | 12/2002 | Ellis et al. |
| 2003/0018379 A1 | 1/2003 | Knudson et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0073973 A1 | 4/2003 | Evans et al. |
| 2003/0078561 A1 | 4/2003 | Gambale et al. |
| 2003/0105514 A1 | 6/2003 | Phelps et al. |
| 2003/0120195 A1 | 6/2003 | Milo et al. |
| 2003/0149474 A1 | 8/2003 | Becker |
| 2003/0158573 A1 | 8/2003 | Gittings et al. |
| 2003/0181938 A1 | 9/2003 | Roth et al. |
| 2003/0191449 A1 | 10/2003 | Nash et al. |
| 2003/0195457 A1 | 10/2003 | LaFontaine et al. |
| 2003/0195458 A1 | 10/2003 | Phelps et al. |
| 2003/0216679 A1 | 11/2003 | Wolf et al. |
| 2003/0229366 A1 | 12/2003 | Reggie et al. |
| 2003/0236542 A1 | 12/2003 | Makower |
| 2004/0015225 A1 | 1/2004 | Kim et al. |
| 2004/0019348 A1 | 1/2004 | Stevens et al. |
| 2004/0044392 A1 | 3/2004 | Von Oepen |
| 2004/0059280 A1 | 3/2004 | Makower et al. |
| 2004/0073157 A1 | 4/2004 | Knudson et al. |
| 2004/0073238 A1 | 4/2004 | Makower |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0088042 A1 | 5/2004 | Kim et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0133154 A1 | 7/2004 | Flaherty et al. |
| 2004/0133225 A1 | 7/2004 | Makower |

FOREIGN PATENT DOCUMENTS

| | | |
|---|---|---|
| EP | 0 815 798 A2 | 7/1997 |
| EP | 0 829 239 A1 | 8/1997 |
| EP | 0 792 624 A1 | 9/1997 |
| EP | 0 797 957 A1 | 10/1997 |
| EP | 0 797 958 A1 | 10/1997 |
| EP | 0 799 604 A1 | 10/1997 |
| EP | 0 801 928 A1 | 10/1997 |
| EP | 0 836 834 A2 | 10/1997 |
| EP | 0 876 796 A2 | 5/1998 |
| EP | 0 853 921 A2 | 7/1998 |
| EP | 0 858 779 A1 | 8/1998 |
| EP | 0 876 803 A2 | 11/1998 |
| EP | 0 888 750 A1 | 1/1999 |
| EP | 0 895 752 A1 | 2/1999 |
| EP | 0 934 728 A2 | 8/1999 |
| EP | 1 020 166 A1 | 7/2000 |
| EP | 1 027 870 A1 | 8/2000 |
| EP | 1 088 564 A1 | 4/2001 |
| EP | 1 097 676 A1 | 5/2001 |
| EP | 1 166 721 A2 | 1/2002 |
| EP | 0 959 815 A1 | 12/2002 |
| EP | 1 112 097 A1 | 6/2003 |

| | | |
|---|---|---|
| GB | 2 316 322 B | 2/1998 |
| WO | WO 96/32972 | 10/1996 |
| WO | WO 96/35469 | 11/1996 |
| WO | WO 96/39962 | 12/1996 |
| WO | WO 96/39964 | 12/1996 |
| WO | WO 96/39965 | 12/1996 |
| WO | WO 97/13463 | 4/1997 |
| WO | WO 97/13471 | 4/1997 |
| WO | WO 97/27893 | 8/1997 |
| WO | WO 97/27897 | 8/1997 |
| WO | WO 97/27898 | 8/1997 |
| WO | WO 97/32551 | 9/1997 |
| WO | WO 97/43961 | 11/1997 |
| WO | WO 98/03118 | 1/1998 |
| WO | WO 98/06356 | 2/1998 |
| WO | WO 98/08456 | 3/1998 |
| WO | WO 98/10714 | 3/1998 |
| WO | WO 98/16161 | 4/1998 |
| WO | WO 98/24373 | 6/1998 |
| WO | WO 98/25533 | 6/1998 |
| WO | WO 98/38916 | 9/1998 |
| WO | WO 98/38925 | 9/1998 |
| WO | WO 98/38939 | 9/1998 |
| WO | WO 98/38941 | 9/1998 |
| WO | WO 98/39038 | 9/1998 |
| WO | WO 98/46115 | 10/1998 |
| WO | WO 98/46119 | 10/1998 |
| WO | WO 98/49964 | 11/1998 |
| WO | WO 98/57590 | 12/1998 |
| WO | WO 98/57591 | 12/1998 |
| WO | WO 98/57592 | 12/1998 |
| WO | WO 99/07296 | 2/1999 |
| WO | WO 99/08624 | 2/1999 |
| WO | WO 99/15220 | 4/1999 |
| WO | WO 99/17671 | 4/1999 |
| WO | WO 99/17683 | 4/1999 |
| WO | WO 99/21490 | 5/1999 |
| WO | WO 99/21510 | 5/1999 |
| WO | WO 99/22655 | 5/1999 |
| WO | WO 99/22658 | 5/1999 |
| WO | WO 99/25273 | 5/1999 |
| WO | WO 99/27985 | 6/1999 |
| WO | WO 99/35977 | 7/1999 |
| WO | WO 99/35979 | 7/1999 |
| WO | WO 99/35980 | 7/1999 |
| WO | WO 99/36000 | 7/1999 |
| WO | WO 99/36001 | 7/1999 |
| WO | WO 99/38459 | 8/1999 |
| WO | WO 99/40853 | 8/1999 |
| WO | WO 99/40868 | 8/1999 |
| WO | WO 99/40963 | 8/1999 |
| WO | WO 99/44524 | 9/1999 |
| WO | WO 99/48545 | 9/1999 |
| WO | WO 99/48549 | 9/1999 |
| WO | WO 99/49793 | 10/1999 |
| WO | WO 99/49910 | 10/1999 |
| WO | WO 99/51162 | 10/1999 |
| WO | WO 99/53863 | 10/1999 |
| WO | WO 99/55406 | 11/1999 |
| WO | WO 99/60941 | 12/1999 |
| WO | WO 99/62430 | 12/1999 |
| WO | WO 00/09195 | 2/2000 |
| WO | WO 00/12029 | 3/2000 |
| WO | WO 00/13722 | 3/2000 |
| WO | WO 00/15146 | 3/2000 |
| WO | WO 00/15147 | 3/2000 |
| WO | WO 00/15148 | 3/2000 |
| WO | WO 00/15149 A1 | 3/2000 |
| WO | WO 00/15275 | 3/2000 |
| WO | WO 00/18302 | 4/2000 |
| WO | WO 00/18323 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | WO 00/21436 | 4/2000 |
| WO | WO 00/21461 | 4/2000 |
| WO | WO 00/21463 | 4/2000 |
| WO | WO 00/24449 | 5/2000 |
| WO | WO 00/33725 | 6/2000 |
| WO | WO 00/35376 | 6/2000 |
| WO | WO 00/36997 | 6/2000 |
| WO | WO 00/41632 | 7/2000 |
| WO | WO 00/41633 | 7/2000 |
| WO | WO 00/43051 | 7/2000 |
| WO | WO 00/45711 | 8/2000 |
| WO | WO 00/45886 | 8/2000 |
| WO | WO 00/49952 | 8/2000 |
| WO | WO 00/49954 | 8/2000 |
| WO | WO 00/49956 | 8/2000 |
| WO | WO 00/54660 | 9/2000 |
| WO | WO 00/54661 | 9/2000 |
| WO | WO 00/56224 | 9/2000 |
| WO | WO 00/56225 | 9/2000 |
| WO | WO 00/56387 | 9/2000 |
| WO | WO 00/66007 | 11/2000 |
| WO | WO 00/66009 | 11/2000 |
| WO | WO 00/71195 A1 | 11/2000 |

OTHER PUBLICATIONS

Wakabayashi et al.; *Myocardial boring for the ischemic heart*, International Cardiovascular Society; vol. 95 (Nov. 1967), pp. 743–752.

Lary et al.; *Myocardial revascularization experiments using the epicardium*; Arch. Surg., vol. 98 (Jan. 1969) pp. 69–72.

Kuzela et al.; *Experimental evaluation of direct transventricular revascularization*; Journal of Thoracic and Cardiovascular Surgery, vol. 57 (Jan.–Jun. 1969) pp. 770–773.

Anabtawi et al.; *Experimental evaluation of myocardial tunnelization as a method of myocardial revascularization*; Journal of Thoracic and Cardiovascular Surgery, (Nov. 1969) pp. 638–646.

Palmaz et al.; *Expandable intrahepatic portacaval shunt stents in dogs with chronic portal hypertension*; AJR, vol. 147 (Dec. 1986) pp. 1251–1254.

Palmaz et al.; *Expandable intrahepatic portacaval shunt stents: early experience in the dog*; AJR, vol. 145 (Oct. 1985) pp. 821–825.

Gardner et al.; *An experimental anatomic study of indirect myocardial revascularization*; Journal of Surgical Research, vol. 11 (1971) pp. 243–247.

Lary et al.; *A method for creating a coronary–myocardial artery*Surgery, vol. 59 (Jun. 1966) pp. 1061–10640.

Ahmed et al.; *Silent left coronary artery–cameral fistula: probable cause of myocardial ischemia*; American Heart Journal, vol. 104 (Oct. 1982) pp. 869–870.

Zemel et al.; *Percutaneous transjugular portosystemic shunt*, JAMA, vol. 266 (Jul. 1991) pp. 390–393.

Richter et al.; *Transjugular intrahepatic portacaval stent shunt: preliminary clinical results*; RSNA–SCVIR, vol. 174 (Mar. 1990) pp. 1027–1030.

Massimo et al., Myocardial, *Revascularization by a New Method of Carrying Blood Directly from the left ventricular cavity into the Coronary Circulation*, from the S. Maria.Nuova Hospital: Surgeon–in–Chief, Tominiaso Greco, M.D., received for publication Oct. 16, 1956, J. Thoracic Surgery vol. 34: (1957) pp. 257–264.

Archie, Joseph P. Jr., *Intramyocardial Pressure: Effect of Preload on Transmural Distribution of Systolic Coronary Blood Flow*, The American Journal of Cardiology, vol. 35, (Jun. 1975), pp. 904–911.

Burch, et al., An International Publication for the Study of the Circulation, American Heart Journal, (Jan. 1980), pp. 8–9.

Lee et al., *Effects of laser Irradiation delivered by flexible fiberoptic system on the left ventricular internal myocardium*, American Heart Journal, (Sep. 1983), vol. 106, No. 3, pp. 587–590.

Galioto, et al., *Right coronary artery to left ventricle fistula*, AHJ, vol. 82, No. 1, (Jul. 1971), No. 1, p. 93–97.

Levinsky, et al., *The Revival of the Horseshoe Graft*, The Thoracic and Cardiovascular Surgeon, vol. 27, No. 5, (Oct. 1979), pp. 281–344.

Medical Industry Today Headline News, Device and Diagnostics, (Jul. 17, 1998), Article #07179802, Article is 349 words long, pp. 1–2.

Medical Industry Today Headline News, Financial News, (Jul. 17, 1998), Article 07179808, article is 560 words long, pp. 1–2.

Munro, et al., *The possibility of myocardial revascularization by creation of a left ventriculocoronary artery fistula*, The Journal of Thoracic and Cardiovascular Surgery, vol. 58, (1969), pp. 25–32.

Bohning, et al., *The Thebesian Vessels as a Source of Nourishment for the Myocardium*, From the Cardiovascular Laboratory, Department of Physiology, Michael Reese Hospital, Chicago, Received for publication on Jun. 23, 1933.

Oesterle, et al., *Catheter–Based Coronary Bypass: A Development Update*, Catheterization and Cardiovascular Interventions, vol. 58, (2003), pp. 212–218.

Goldman, et al. *Experimental Methods for Producing a Collateral Circulation to the Heart Directly from the Left Ventricle*, J. Thoracic Surgery, vol. 31, No. 3 (Mar. 1956) pp. 364–374.

Cohen et al., *Alternative Approaches to Coronary Revascularization*, Current International Cardiology Reports, vol. 1 (1999), pp. 138–146.

* cited by examiner

TRANSMYOCARDIAL IMPLANT WITH FLOW REDUCTION

CROSS-REFERENCE TO RELATED APPLICATIONS

This is a continuation application of application Ser. No. 09/304,730, filed May 4, 1999, now U.S. Pat. No. 6,409,697 B2, the entirety of which is incorporated herein by reference.

BACKGROUND OF THE INVENTION

1. Field of the Invention

This invention pertains to an implant for passing blood flow directly between a chamber of the heart and a coronary vessel. More particularly, this invention pertains to such an implant with an enhance design for reducing a likelihood of damage to a coronary vessel from a high velocity blood flow discharge.

2. Description of the Prior Art

Commonly assigned U.S. Pat. No. 5,755,682 and PCT International Publication No. WO 98/06356 teach an implant for defining a blood flow conduit directly from a chamber of the heart to a lumen of a coronary vessel. An embodiment disclosed in the aforementioned patent and application teaches an L-shaped implant. The implant is a conduit having one leg sized to be received within a lumen of a coronary artery and a second leg sized to pass through the myocardium and extend into the left ventricle of the heart. As disclosed in the above-referenced patent and application, the conduit remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, entitled "Transmyocardial Implant", and filed in the name of inventors Katherine S. Tweden, Guy P. Vanney and Thomas L. Odland, teaches an implant such as that shown in the aforementioned '682 patent with an enhanced fixation structure. The enhanced fixation structure includes a fabric surrounding at least a portion of the conduit to facilitate tissue growth on the exterior of the implant.

Implants such as those shown in the aforementioned patent and applications include a portion to be placed within a coronary vessel and a portion to be placed within the myocardium. When placing a portion of the implant in the coronary vessel, the vessel is incised a length sufficient to insert the implant. When placed within the coronary vessel, the implant discharges flow axially into the vessel. A portion of an interior surface of the implant portion in the vessel acts as a deflection surface to prevent direct impingement of high velocity blood flow on a vessel wall.

The L-shaped implant described in the foregoing is preferably placed through a surgical procedure (open chest or minimally invasively). The suitability of an implant for minimally invasive or percutaneous procedures is influenced, at least in part, by the external size and shape of the implant. The size can be reduced and shape enhanced by elimination of the vessel portion of the foregoing designs.

SUMMARY OF THE INVENTION

According to a preferred embodiment of the present invention, a transmyocardial implant is disclosed for establishing a blood flow path through a heart wall between a heart chamber and a lumen of a coronary vessel on the heart wall. The implant includes a hollow conduit having an open first end and an open second end. The conduit is dimensioned so as to extend at least from the vessel through said heart wall and into said chamber. The conduit has a conduit wall defining a blood flow pathway within an interior of said conduit between the first and second ends. The first and second ends are mutually positioned for the first end to reside within the vessel and opposing a wall of the vessel when the conduit is placed within the heart wall with the second end protruding into the chamber. The conduit wall is formed of a material sufficiently rigid to resist deformation and closure of the pathway in response to contraction of the heart wall. A flow restriction is formed in the pathway for reducing a discharge velocity of blood flow discharged from the first end.

DESCRIPTION OF THE PREFERRED EMBODIMENT

Figure 1:
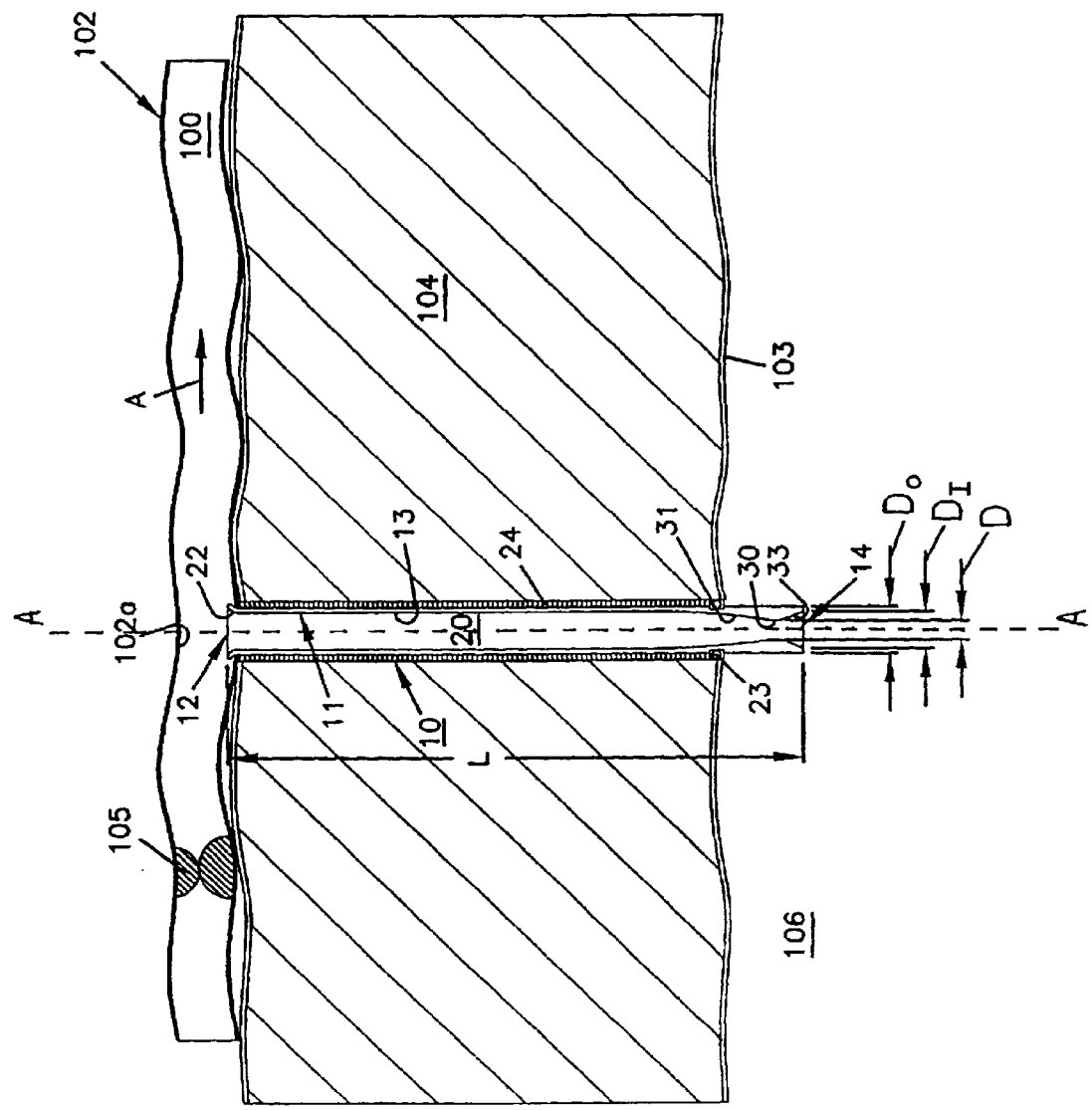
FIG. 1 is a schematic cross-sectional view of an implant according to the present invention in place in a heart wall to define a blood flow path from a left ventricle to a coronary artery distal to an obstruction.

With reference to FIG. 1, an implant 10 is shown including a straight elongate, generally cylindrical tube or conduit 11. The conduit 11 may be formed of titanium or other rigid biocompatible material such as pyrolytic carbon or may be titanium coated with pyrolytic carbon. Preferably, the interior wall 13 of the conduit 11 is polished to a high degree of polish to reduce the likelihood of thrombus formation on the wall. The material of the conduit 11 is preferably a rigid material in order to withstand contraction forces of the heart wall, as will be described.

In the preferred embodiment, the tube 11 will have an outside diameter $D_o$ of about 1 to 3 millimeters and an internal diameter $D_1$ of about 0.5 to 2.5 millimeters to provide a wall thickness of about 0.5 millimeters. By way of non-limiting example, a specific $D_o$ may be 2.5 millimeters and a specific $D_1$ may be 2.0 millimeters.

The size range given permits insertion of the conduit into a coronary vessel to be bypassed. Commonly, such vessels in an adult human have internal diameters of 1 to 3 millimeters when under the influence of normal pressurized blood flow.

The tube 11 has a first open end 12 which is sized to be received within the lumen of a coronary vessel such as the lumen 100 of a coronary artery 102 illustrated in FIG. 1. As used in this application, the term "vessel" refers to veins or arteries. The present invention is described with reference to bypassing a coronary artery with blood from a left ventricle. The invention is equally applicable to forming a blood flow path from other heart chamber to any other coronary vessel.

The conduit 11 has a second open end 14. The conduit 11 is sized to extend from the coronary artery 102 directly through the heart wall 104 and protrude into the left ventricle 106 of a patient's heart. Preferably, the end 14 protrudes at least about 5 millimeters from an inner surface 103 of the heart wall 104 during maximum heart wall thickness during systole. Heart wall thickness varies from patient to patient and among locations on the heart. In a preferred embodiment of forming a flow path from the left ventricle to a coronary artery of an adult human, the length L of the conduit (measured as the axial distance between ends 12 and 14) will be between about 10 and 30 millimeters. With the foregoing specific example, for a heart wall 104 having a maximum systolic thickness of 20 millimeters, the length L of the conduit 11 is 25 millimeters.

The openings 12, 14 communicate with an interior 20 of the conduit 11. Therefore, blood can freely flow through the conduit 11 between the left ventricle 106 and the lumen 100 of the coronary artery 102.

At first opening 12, the conduit 11 is outwardly flared at 22 to act as a stop to limit insertion of the implant 10 into the heart wall 104. Further, the flaring 22 acts as a smooth flow path for guiding blood flow out of end 12.

As mentioned, the tube 11 is preferably formed of titanium or other smooth biocompatible material in order to resist thrombus formation on the inner surface 13 of the conduit 11. Titanium is a presently preferred material due its long-term use in the cardiovascular industry. Further, titanium is sufficiently rigid to withstand deformation forces caused by contraction of the heart wall 104 to avoid deformation of the tube 11 so that the tube 11 remains open during both diastole and systole. Also, the tube 11 is solid on its cylindrical inner surface 13. Therefore, highly thrombogenic material from the heart wall 104 cannot pass into and contaminate the interior 20 of the conduit 11.

While tissue will adhere to titanium, the adhesion may be inadequate when subjected to the shearing contracting forces of the heart wall 104 due to the relative smoothness of extruded titanium. Therefore, a completed implant 10 includes a sleeve 24 of tissue growth-inducing material secured to an exterior surface of the conduit 11. The sleeve 24 is attached to the conduit 11 by a suture 23 tightly surrounding both the sleeve 24 and conduit 11.

The sleeve 24 surrounds the exterior surface of the tube 11 and is recessed back from both of ends 12, 14 so that after placement the sleeve 24 resides solely in the heart wall 104 (although slight protrusion of sleeve 24 into the left ventricle can be tolerated). It is desired the sleeve not be so closely positioned near open ends 12, 14 such that tissue growth on the sleeve 24 can grow over and occlude the open ends 12, 14. It is anticipated that tissue growth on and into the sleeve 24 could result in a buildup of tissue beyond the sleeve 24 to a thickness of about at least 1 millimeter. It is desirable that such tissue growth does not extend over ends 12, 14. Accordingly, the sleeve 24 is spaced from ends of the tube 11 by a distance greater than an anticipated thickness of tissue growth extension beyond the sleeve 24.

The sleeve 24 is selected to induce tissue growth and attachment. Preferably, the sleeve 24 is formed of a fabric having biocompatible fibers defining interstitial spaces to receive tissue growth. An example of such a fabric is polyethylene terephthalate (such as polyester fabric sold by DuPont Company under the trademark DACRON®). Such a fabric permits rapid tissue integration into the fabric thereby anchoring the fabric and, hence, the tube 11 to the patient's tissue.

While a fabric tissue growth inducing material is illustrated, other materials could be used. For example, the tissue growth inducing material could be sintered metal on the external surface of the tube 11. Sintered metal results in a porous surface to receive tissue growth. The area of the sintered metal will be spaced from ends 12, 14 to prevent tissue accumulation on the sintered area from growing over and blocking 12, 14. Alternatively, the exterior surface of the tube 11 can be roughened. The roughening can be in the form of a knurling or other roughened surface due to sandblasting or the application of sinter beads. The roughening results in surface protrusions and pitting, around which tissue may grow.

The implant 10 is placed with the first end 12 placed within the artery lumen 100 distal to an obstruction 105. Normal nourishing blood flow is in the direction of arrow A. The implant 10 passes through the heart wall 104 with the second end 14 positioned within the left ventricle 106 and spaced from the inner surface 103 of the heart wall 104 by 5 millimeters during periods of maximum heart wall thickness. The sleeve 24 is positioned opposing the heart wall 104 so that tissue from the heart wall 104 can grow into the sleeve 24.

With the positioning thus described, the first opening 12 opposes a wall 102a of the artery 102. As a result, blood discharged from the opening 12 impinges directly upon the arterial wall 102a.

The artery wall 102a is a fragile layer of cells and fibers. Direct impingement of blood flow on the wall 102a can damage the artery wall 102a. As a healing response to such damage, a cellular matrix may develop and proliferate to such an extent that opening 12 or lumen 100 could occlude.

The present invention reduces the velocity of blood flow through the opening 12. Specifically, a flow restriction in the form of a narrowing 30 is placed within the conduit 11. The restriction 30 reduces blood flow below a velocity which would otherwise cause occluding trauma to the artery wall 102a.

With the specific example given, the restriction 30 results in a narrow interior diameter D of about 0.5 millimeters. The narrow restriction 30 is positioned about 8 millimeters from end 14. The restriction 30 is formed by a venturi constriction formed within the conduit 11 adjacent end 14. The venturi may be formed by machining the conduit 11 from a solid blank of titanium. The venturi 30 has a shallow ramp 31 on a downstream side to avoid turbulence. Since an upstream side 33 is adjacent end 14, turbulence during reverse flow is not a serious concern.

With the restriction 30 as described, flow velocity out of end 12 is reduced below a level which would otherwise cause occluding trauma to the artery wall 102a. By avoiding such trauma, a straight implant 10 can be provided which is more susceptible to minimally invasive and percutaneous implantation as well as being suitable for traditional surgical approaches.

Preferably, the blood flow velocity from end 12 is reduced to a velocity of normal blood flow within an artery 102 (about 30 ml/min.). Since the left ventricle 106 has a high maximum pressure, the pressure differential between the ventricle 106 and artery lumen 100 results in a higher than normal blood flow rate in the absence of the restriction 30.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims appended hereto. For example, in the preferred embodiment shown, the tube 11 is a cylinder with circular cross-section. The tube 11 could have an oval cross-section at end 12 to provide a larger flow area and further reduce flow velocity. Also, while the tube 11 is preferably straight, the tube 11 could be bent so that the direction of blood flow from end 12 is not perpendicular to the arterial blood flow direction A.

What is claimed:

1. A transmyocardial implant for establishing a blood flow path through a heart wall between a heart chamber and a lumen of a coronary vessel comprising:

a hollow conduit having an open first end and an open second end, said conduit sized to extend at least from said vessel through said heart wall and into said chamber, said conduit having a conduit wall defining a blood flow pathway within an interior of said conduit between said first and second ends;

said first and second ends mutually positioned for said first end to reside within said vessel and opposing a wall of said vessel when said conduit is placed within said heart wall with said second end protruding into said chamber;

said conduit wall formed of a material sufficiently rigid to resist deformation and closure of said pathway in response to contraction of said heart wall;

a flow restriction formed in said pathway configured to reduce a discharge velocity of blood flow discharged from said first end, the flow restriction defined by a variation in a cross-sectional area of the blood flow defined by the conduit wall.

2. A transmyocardial implant according to claim 1 further comprising a tissue growth inducing material surrounding said conduit wall.

3. A transmyocardial implant according to claim 2 wherein said tissue growth inducing material includes a plurality of fibers defining a plurality of interstitial spaces for receiving tissue growth and said tissue growth inducing material is biocompatible.

4. A transmyocardial implant according to claim 3 wherein said tissue growth inducing material is a polyester fabric.

5. A transmyocardial implant according to claim 2 wherein said tissue growth inducing material include a porous layer on said exterior of said conduit.

6. A transmyocardial implant according to claim 5 wherein said tissue growth inducing material includes a sintered layer.

7. A transmyocardial implant according to claim 2 wherein an external area of said conduit surrounded by said tissue growth inducing material is abraded.

8. A transmyocardial implant according to claim 1 wherein said flow restriction is a narrowing in said pathway positioned between enlarge cross-sectional sectional areas of said pathway.

9. A transmyocardial implant according to claim 8 wherein said pathway has a substantially straight longitudinal axis between said first and second ends.

10. A transmyocardial implant according to claim 1, wherein the conduit wall defines a first inner diameter transition extending from a region of maximum flow restriction towards said first end and a second inner diameter transition extending from said region of maximum flow restriction towards said second end.

11. A transmyocardial implant according to claim 10, wherein said first diameter transition defines a smaller angle of transition relative to a central reference axis that said second inner diameter transition.

12. A transmyocardial implant according to claim 1, wherein said flow restriction is configured to reduce a blood flow velocity such that said blood flow velocity is less than an occluding trauma including velocity.

13. A transmyocardial implant according to claim 1, wherein said heart chamber is a left ventricle.

14. A transmyocardial implant according to claim 1, wherein said coronary vessel is a coronary vein.

15. A transmyocardial implant according to claim 1 wherein said conduit is sized for said first end to extend into said chamber beyond said heart wall.

16. A method for establishing a blood flow path through a heart wall between a heart chamber and a lumen of a coronary vessel on said heart wall, said method comprising:

forming a blood flow path from said vessel through said heart wall and into said chamber;

maintaining said blood flow path open during both systole and diastole; and restricting blood flow through said pathway to reduce a discharge velocity of blood flow discharged into said vessel.

17. The method of claim 16, wherein the conduit wall defines a first inner diameter transition extending from a region of maximum flow restriction towards said first end and a second inner diameter transition extending from region of maximum flow restriction towards said second end.

18. The method of claim 17, wherein said first diameter transition defines a smaller angle of transition relative to a central reference axis that said second inner diameter transition.

19. The method of claim 16, further comprising maintaining the blood flow path open during both systole and diastole.

20. The method of claim 16, further comprising restricting the blood flow through the pathway, via flow restriction, so as to reduce the blood flow velocity to below an occluding trauma inducing velocity.

21. The method of claim 16, further comprising placing a tissue growth inducing material on the conduit wall.

22. The method of claim 16, wherein the coronary vessel is a coronary vein.

23. The method of claim 16, wherein the heart chamber is a left ventricle.

* * * * *

UNITED STATES PATENT AND TRADEMARK OFFICE
CERTIFICATE OF CORRECTION

PATENT NO. : 6,916,304 B2
DATED : July 12, 2005
INVENTOR(S) : Robert A. Eno et al.

It is certified that error appears in the above-identified patent and that said Letters Patent is hereby corrected as shown below:

Title page,
Item [73], Assignee, "Merrimac" should read -- Merrimack --.

Column 5,
Line 30, "include" should read -- includes --;
Line 39, "enlarge" should read -- enlarged --.

Signed and Sealed this

Eleventh Day of October, 2005

JON W. DUDAS
*Director of the United States Patent and Trademark Office*